US012042577B2

(12) United States Patent
Inouye et al.

(10) Patent No.: US 12,042,577 B2
(45) Date of Patent: Jul. 23, 2024

(54) MEDICAL DEVICES HAVING INCREASED FATIGUE RESISTANCE

(71) Applicant: BOSTON SCIENTIFIC SCIMED, INC., Maple Grove, MN (US)

(72) Inventors: Joshua Mark Inouye, Maple Grove, MN (US); Brian T. Berg, St. Paul, MN (US); Graham Krumpelmann, Stillwater, MN (US); Ted William Pelzer, Otsego, MN (US); Kelsey Rae Cooper, Andover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 182 days.

(21) Appl. No.: 17/512,248

(22) Filed: Oct. 27, 2021

(65) Prior Publication Data

US 2022/0125997 A1 Apr. 28, 2022

Related U.S. Application Data

(60) Provisional application No. 63/106,162, filed on Oct. 27, 2020.

(51) Int. Cl.
*A61L 27/50* (2006.01)
*A61L 27/06* (2006.01)
*C22F 1/00* (2006.01)
*C22F 1/10* (2006.01)

(52) U.S. Cl.
CPC .............. *A61L 27/50* (2013.01); *A61L 27/06* (2013.01); *C22F 1/006* (2013.01); *A61L 2400/16* (2013.01); *A61L 2430/20* (2013.01)

(58) Field of Classification Search
None
See application file for complete search history.

(56) References Cited

U.S. PATENT DOCUMENTS

| 5,662,294 A * | 9/1997 | Maclean | B63B 1/28 114/140 |
| 6,149,742 A * | 11/2000 | Carpenter | C22F 1/006 337/140 |
| 6,612,012 B2 * | 9/2003 | Mitelberg | A61F 2/915 148/426 |
| 9,622,862 B2 | 4/2017 | Lashinski et al. | |
| 9,687,346 B2 | 6/2017 | Migliazza et al. | |
| 2002/0189727 A1 * | 12/2002 | Peterson | A61F 2/0108 148/563 |
| 2004/0039414 A1 * | 2/2004 | Carley | C22C 19/007 606/213 |

(Continued)

OTHER PUBLICATIONS

Coan et al: "Effect of Cooling Rates on the Transformation Behavior and Mechanical Properties of a Ni-Rich NiTi Alloy", Shap. Mem. Superelasticity, vol. 3, pp. 315-321, 2017.

(Continued)

*Primary Examiner* — George Wyszomierski
(74) *Attorney, Agent, or Firm* — Seager, Tufte & Wickhem LLP

(57) ABSTRACT

Example medical devices and methods of making example medical devices are disclosed. An example medical device includes a frame configured to be secured to cardiac tissue, wherein the frame includes a fatigue resistant nickel-titanium alloy that is heat set at a temp in the range of 450-550 degrees Celsius.

4 Claims, 3 Drawing Sheets

(56) References Cited

U.S. PATENT DOCUMENTS

| | | | |
|---|---|---|---|
| 2004/0216814 A1* | 11/2004 | Dooley | A61L 31/14 |
| | | | 148/563 |
| 2010/0107628 A1* | 5/2010 | Schaffer | C22C 19/007 |
| | | | 60/527 |
| 2017/0135816 A1 | 5/2017 | Lashinski et al. | |
| 2018/0311406 A1 | 11/2018 | Francis et al. | |
| 2020/0046878 A1* | 2/2020 | Kim | A61F 2/915 |

OTHER PUBLICATIONS

Confluent Medical Technologies, "Martensite/R-phase Superelasticity and its Implications to Nitinol Durability", 33 pages, 2017.

Duerig et al; "The Influence of the R-Phase on the Superelastic Behavior of NiTi", Shap. Mem. Superelasticity, vol. 1, pp. 153-161, 2015.

Pelton et al; "Effects of Thermal Cycling on Microstructure and Properties in Nitinol", Materials Science and Engineering A 532, pp. 130-138, 2012.

Pelton; "Nitinol Fatigue: A Review of Microstructure and Mechanisms", Journal of Materials Engineering and Performance, 5 pages, Published online Feb. 16, 2011.

Senthilnathan et al; Effect of Tensile and Compressive Pre-Strains on Superelastic Diamond Surrogates, Shape Memory and Superelastic Technologies Conference and Exposition, Confluent Medical Technologies, 5 pages, 2017.

International Search Report and Written Opinion dated Feb. 18, 2022 for International Application No. PCT/US2021/056851.

\* cited by examiner

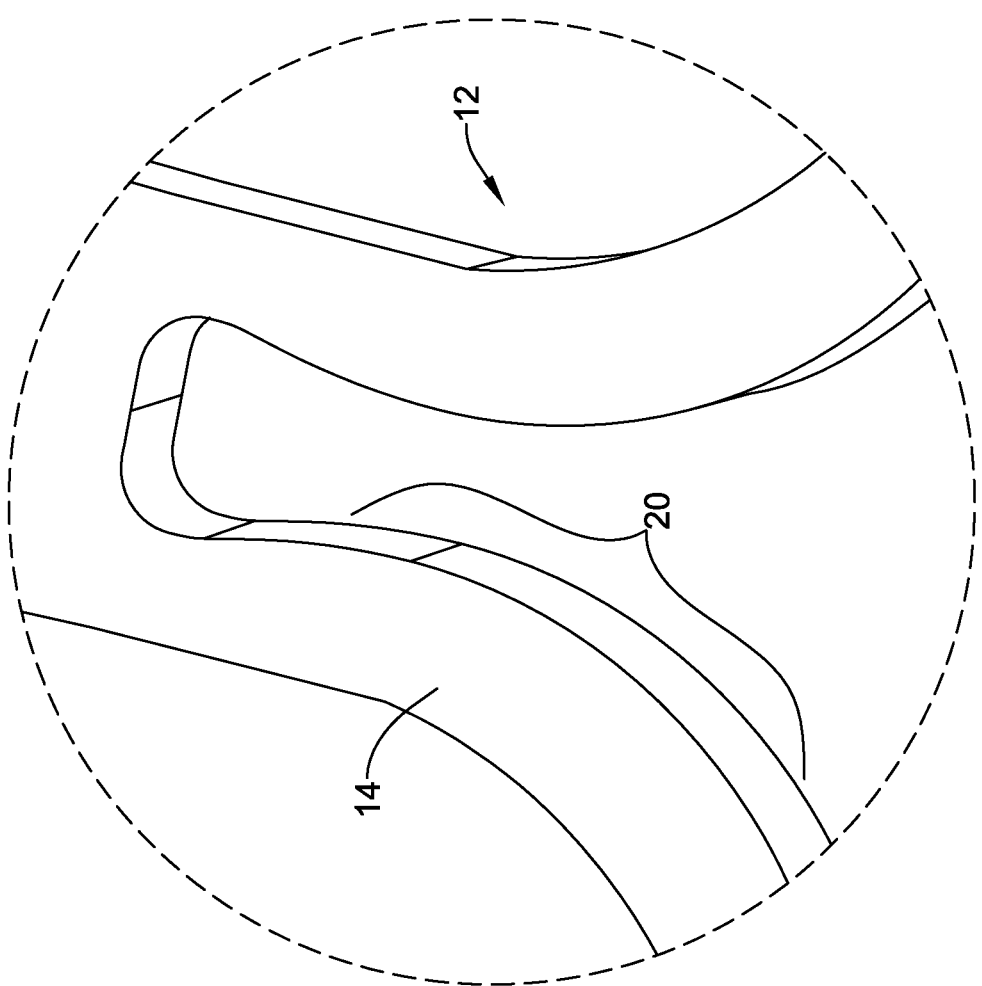

MEDICAL DEVICES HAVING INCREASED FATIGUE RESISTANCE

CROSS REFERENCE TO RELATED APPLICATIONS

This application claims the benefit of and priority to U.S. Provisional Patent Application Ser. No. 63/106,162 filed on Oct. 27, 2020, the disclosure of which is incorporated herein by reference.

TECHNICAL FIELD

The present disclosure pertains to medical devices, and methods for manufacturing medical devices. More particularly, the present disclosure pertains to cardiovascular implants including a heart valve repair device and methods for manufacturing and using such devices.

BACKGROUND

A wide variety of medical devices such as heart valve repair devices, heart valve repair devices (e.g., annuloplasty rings), self-expanding stents, occlusion devices, cardiovascular filters (e.g., IVC filters), etc. have been developed to treat a variety of cardiovascular conditions. Because medical devices placed in the heart must deliver their therapeutic function while not interfering with or harming other native functions, it can be desirable to have particular performance features in the medical device. A number of different structures and assemblies for medical devices such as heart valves are known, each having certain advantages and disadvantages. However, there is an ongoing need to provide alternative structures and assemblies.

BRIEF SUMMARY

This disclosure provides design, material, manufacturing method, and use alternatives for medical devices. An example medical device includes a frame configured to be secured to cardiac tissue, wherein the frame includes a fatigue resistant nickel-titanium alloy that is heat set at a temp in the range of 450-550 degrees Celsius.

Alternatively or additionally to any of the embodiments above, wherein the frame is further processed by flexing the frame through at least one pre-strain cycle.

Alternatively or additionally to any of the embodiments above, wherein the frame is further processed by heat setting the device between a temperature of 150-350 degrees Celsius over a time period of at least 24 to 105 hours.

Alternatively or additionally to any of the embodiments above, wherein the frame is flexed between 10-100 pre-strain cycles.

Alternatively or additionally to any of the embodiments above, wherein flexing the frame between 10 and 100 pre-strain cycles occurs at a temperature of 50-75 degrees Celsius.

Alternatively or additionally to any of the embodiments above, wherein the frame is further processed by heat setting the device between a temperature of 150-350 degrees Celsius over a time period of at least 24 to 105 hours, and wherein the frame is further processed by flexing the frame through at least one pre-strain cycle.

Alternatively or additionally to any of the embodiments above, wherein the frame is further processed by flexing the frame between 10-100 pre-strain cycles.

Alternatively or additionally to any of the embodiments above, wherein processing the device between a temperature of 150-350 degrees Celsius over a time period of at least 24 to 105 hours induces the nickel-titanium alloy to have a R-phase when the frame is at a temperature between 35-39 degrees Celsius.

Alternatively or additionally to any of the embodiments above, wherein the medical device includes an annuloplasty ring.

Another heart valve repair device includes a frame configured to be secured to cardiac tissue, wherein the frame includes a fatigue resistant nickel-titanium alloy that is heat set at a temp in the range of 450-550 degrees Celsius, and wherein the frame is further processed by flexing the frame through at least 10-100 pre-strain cycles at a temperature between 50-70 degrees Celsius.

Alternatively or additionally to any of the embodiments above, wherein the frame is further processed by heat setting the device between a temperature of 150-350 degrees Celsius over a time period of at least 24 to 105 hours.

Alternatively or additionally to any of the embodiments above, wherein processing the device between a temperature of 150-350 degrees Celsius over a time period of at least 24 to 105 hours induces the nickel-titanium alloy to have a parent phase of R-phase when the frame is at a temperature between 35-39 degrees Celsius.

Alternatively or additionally to any of the embodiments above, wherein flexing the frame between 10 and 100 pre-strain cycles occurs at a temperature of 50-75 degrees Celsius.

Alternatively or additionally to any of the embodiments above, wherein flexing the frame through at least 10-100 pre-strain cycles at a temperature between 50-70 degrees Celsius further includes flexing the frame at a strain amplitude of between 6-12%.

Alternatively or additionally to any of the embodiments above, wherein the heart valve repair device includes an annuloplasty ring.

An example method of forming a heart valve repair device, may include forming a nickel-titanium allow into a fatigue resistant frame; and heat setting the nickel-titanium frame at a temp in the range of 450-550 degrees Celsius.

Alternatively or additionally to any of the embodiments above, further comprising flexing the frame between 10-100 pre-strain cycles.

Alternatively or additionally to any of the embodiments above, wherein flexing the frame between 10-100 pre-strain cycles further includes flexing the frame at a strain amplitude of between 6-12%.

Alternatively or additionally to any of the embodiments above, further comprising heat setting the frame between a temperature of 150-350 degrees Celsius over a time period of at least 24 to 105 hours.

Alternatively or additionally to any of the embodiments above, wherein heat setting the frame between a temperature of 150-350 degrees Celsius over a time period of at least 24 to 105 hours induces the nickel-titanium alloy to have a R-phase when the frame is at a temperature between 35-39 degrees Celsius.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 3 is a detailed view of a portion of the frame shown in FIG. 2.

Figure 1:
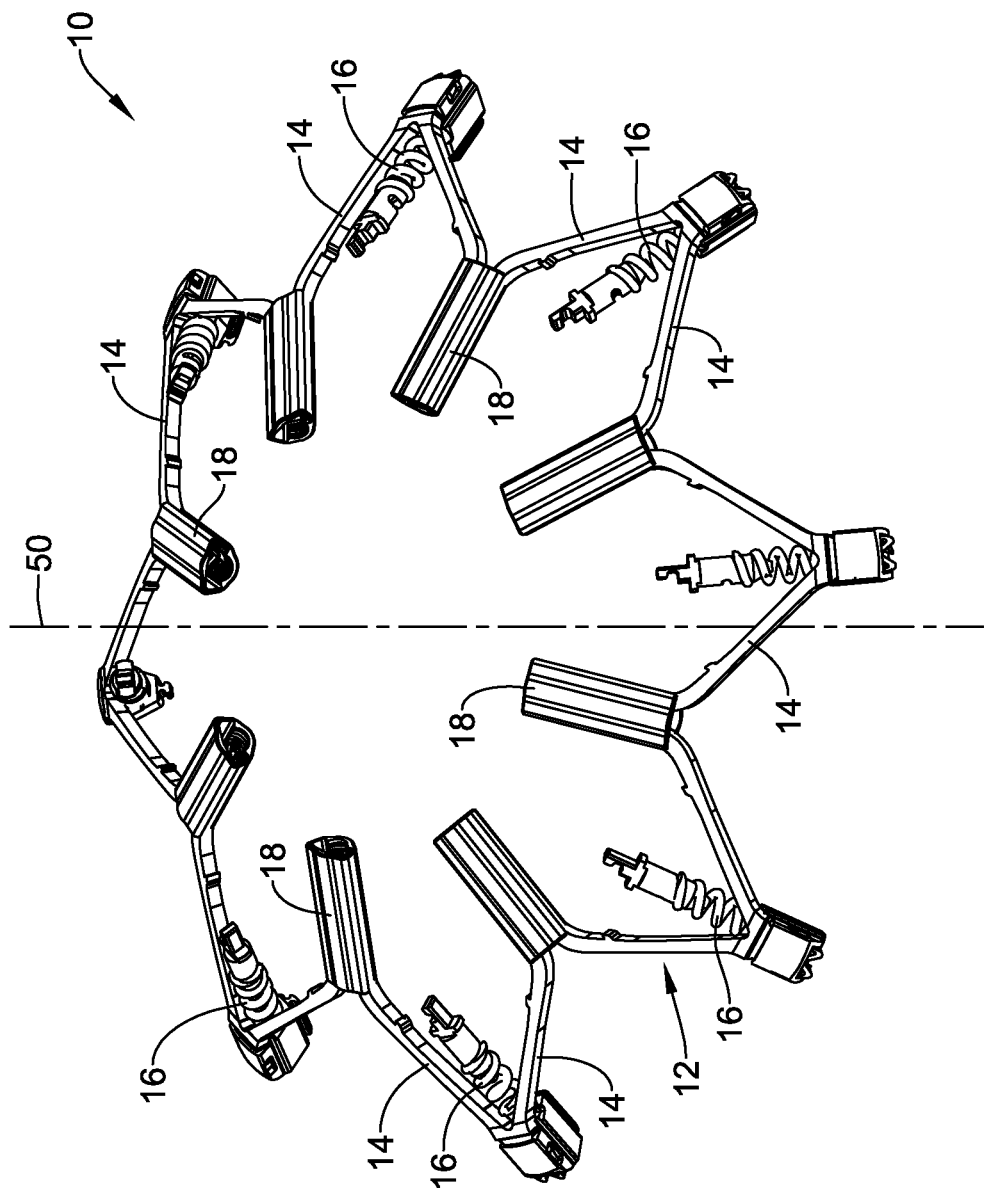
FIG. 1 is a perspective view of an example heart valve repair implant including a frame, collars and anchors.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

The following description should be read with reference to the drawings wherein like reference numerals indicate like elements throughout the several views. The drawings, which are not necessarily to scale, depict illustrative embodiments of the claimed disclosure.

Additionally, although discussed with specific reference to a heart valve repair implant (e.g., an annuloplasty ring) in the particular embodiments described herein, the disclosure may be applicable to a variety of medical devices that are adapted to be advanced into the anatomy of a patient through an opening or lumen. For example, the disclosure may be applicable to heart valve replacement devices and components thereof, self-expanding stents, occlusion devices, cardiovascular filters (e.g., IVC filters, embolic protection filters), guidewires, pressure wires, implantable sensors (e.g., pulmonary artery sensors), cardiac occlusion devices (e.g., atrial septal occluders, ventricular septal occluders, patent foramen ovale occluders, left atrial appendage occluders, paravalvular occluders, etc.), cardiac shunt devices, atrial flow regulators, neuromodulation devices, fixed wire devices, a variety of catheters (e.g., balloon, stent delivery, diagnostic, ablation, steerable, guide, ultrasound imaging, OCT, direct visualization, ureteral, biliary, retrieval balloon, direct injection needle catheters, etc.), drive shafts for rotational devices such as atherectomy catheters and IVUS catheters, endoscopic devices, laproscopic devices, embolic protection devices, spinal or cranial navigational devices, biopsy forceps, retrieval devices and other such devices. Further, the embodiments disclosed herein may be particularly applicable to any medical device having Nitinol components which are subject to cyclical loading. Further yet, while some embodiments may be adapted or configured for use within the vasculature of a patient, other embodiments may be adapted and/or configured for use in other anatomies. It is to be understood that a broad variety of materials, dimensions and structures can be used to construct suitable embodiments, depending on the desired characteristics. The following examples of some embodiments are included by way of example only, and are not intended to be limiting.

The devices of the current disclosure may comprise a heart valve repair device (e.g., an annuloplasty ring), and the medical device may include a frame. The annuloplasty ring, and in particular the frame (and components thereof), may comprise one or more materials that exhibit shape memory behavior, superelastic behavior, or both. These materials can be metal alloys, for example Nitinol.

In general, certain Nitinol alloys can exhibit shape memory or superelastic (or pseudoelastic) behavior, or both. Although nitinol is essentially a binary alloy with nickel and titanium, some superelastic and/or shape memory Ni:Ti alloys can contain additional elements, such as cobalt, iron, chromium, niobium, palladium, copper or vanadium. In addition, some other alloys exhibit shape memory or superelastic behavior or, like some Ni:Ti alloys, both shape memory and superelasticity. Some examples of these alloys are: AgCd, AuCd, AuCu, CuAlNi, CuAuZn, CuSn, CuZn, CuZnSi, CuZnSn, CuZnAl, CuZnGa, CuZnXe, CuAlNi, InTl, NiAl, FePt, FePd, FeMn, Fe3Be, Fe3Pt, FeNiTiCo, and MnCu.

Superelasticity and shape memory are two distinct manifestations of a reversible phase transformation. Superelasticity may be defined as a nonlinear recoverable deformation behavior of Ni—Ti shape memory alloys at temperatures above the austenite finish temperature (Af). The nonlinear deformation arises from the stress induced formation of martensite on loading and the spontaneous reversion of this crystal structure to austenite upon unloading. A shape memory alloy may be defined as a metal which, after an apparent plastic deformation in the martensitic phase, undergoes a thermoelastic change in crystal structure when heated above the austenite finish temperature, resulting in a recovery of the deformation. Without being constrained by the theories presented herein, these concepts will be described in greater detail below.

Regarding the linear elasticity of materials, it can be appreciated that when a stress is applied to linear elastic materials at a relatively constant rate, the material's stress-strain curve may initially be linear until the material reaches its proportional limit. If the stress is further applied to the material after this point, the material may be plastically deformed, whereby the material may not return to its original shape and size when the stress is removed. Thus, with linear elastic materials, the stress-strain curve appears as a substantially straight line within the proportional region (the portion of the curve before the proportional limit). Therefore, when the material is stressed within this proportional region, the strain can increase proportionally, and when the stress is removed, the strain may decrease substantially along the same straight line, substantially back to the origin of the stress-strain graph.

In some cases, linear elastic nitinol may also be distinguishable from superelastic nitinol in that linear elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel, which may accept only about 0.09 to 1.1 percent strain before plastically deforming.

In some embodiments, the linear elastic nickel-titanium alloy does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic nickel-titanium alloy. The mechanical properties of such material may therefore be generally inert to the effect of temperature over this very broad range of temperature. In some embodiments, the mechanical properties of the linear elastic nickel-titanium alloy at ambient or room temperature are substantially the same as the mechanical properties at body temperature, for example, in that they do not display a super-elastic plateau and/or flag region. In other words, across a broad temperature range, the linear elastic nickel-titanium alloy maintains its linear elastic characteristics and/or properties.

In some embodiments, the linear elastic nickel-titanium alloy may be in the range of about 50 to about 60 weight percent nickel, with the remainder being essentially titanium. In some embodiments, the composition is in the range of about 54 to about 57 weight percent nickel.

However, it can be appreciated that in some embodiments, a superelastic alloy, (e.g., a superelastic nitinol) may be used to achieve desired properties and performance characteristics. Specifically, in the case of superelastic metal alloys (SEMAs), the stress-strain curve may be non-linear. This non-linearity may be a product of a phase change that occurs within the alloy when the alloy is being subjected to stress (as opposed to linear elastic materials, which generally do not have substantial phase changes within the elastic region). Some SEMAs may have two solid-state phases that are relevant to superelasticity: the austenite phase and the martensite phase. The austenite phase can be the more ordered phase of these alloys with limited deformation strains without phase change or plastic deformation. The martensite phase can be the lower ordered phase that through twinning is more deformable. The change between these phases is a change in the crystal structure of the metal. Phase change in these materials is generally caused by temperature changes or by external mechanical forces. In some instances, in order to improve the in vivo performance and/or durability of medical devices, it may be desirable to construct the medical devices based on a specific combination of thermal processing and/or pre-strain processing. For example, in some examples described herein, one or more components of a heart valve repair device (e.g., an annuloplasty ring) may be constructed utilizing specific thermal and pre-strain processing techniques. These mechanisms will be discussed in greater detail below.

FIG. 1 illustrates an example heart repair implant (e.g., an annuloplasty ring) 10. The implant 100 may be designed to repair a leaking mitral valve. In particular, the implant 100 may be implanted directly to the annulus of a mitral valve, whereby manipulation of the implant 100 may pull the leaflets of the mitral valve together to re-establish proper mitral valve function.

The implant 100 may include a frame 12. The frame 12 may extend around and partially along a longitudinal axis 50. The axis 50 may be defined by the frame 12. The frame 12 may generally be symmetric with respect to the axis 50. However, the frame 12 need not be symmetric with respect to the axis 50. The frame 12 may be generally circular in shape about the axis 50. However, this is not intended to be limiting. Rather, the frame 12 may be circular, rounded, ellipsoidal, segmented, other shapes, or combinations thereof. The frame 12 may change shape, size, configuration, etc.

The implant 100 may include one or more struts 14. The struts 14 may be elongated members of the frame 12. In some examples, the struts 14 and/or other components of the frame 12 may be formed of an alloy of nickel titanium (e.g., Nitinol). In other examples, the struts 14 and/or other parts of the frame 12 may be formed of other metals, metal alloys, plastics, polymers, composites, other suitable materials, or combinations thereof. Further, FIG. 1 illustrates that the frame 12 may include sixteen struts 14. However, in other examples, there may be fewer or more than sixteen struts 14. For example, in some embodiments, there may be at least two, four, six, eight, ten, twelve, fourteen, eighteen, twenty, twenty-two, twenty-four, twenty-six, twenty-eight, thirty, or more struts 14.

In some examples, the struts 14 may be constructed from a monolithic piece of material. In other embodiments, however, the struts 14 may be separate components that are detachably coupled together by other components of the implant 100. For example, the struts 14 may be held together via various components described herein, such as collars 18, anchors 16, other components, or combinations thereof. In some embodiments, the struts 14 may be attached by hinges, pins, or other suitable means.

As illustrated in FIG. 1, the elongated, middle portions of the struts 14 may have a generally rectangular cross-section but can vary in circumferential width and radial thickness to allow for different beam characteristics and forces applied as the collars are manipulated. "Circumference" as used herein generally refers to a perimeter or boundary and can refer to a circular or other rounded or non-rounded path lying in a plane substantially transverse to the axis, unless otherwise stated. In some embodiments, other configurations and/or cross-sectional shapes of the struts 14 may be implemented.

Figure 2:
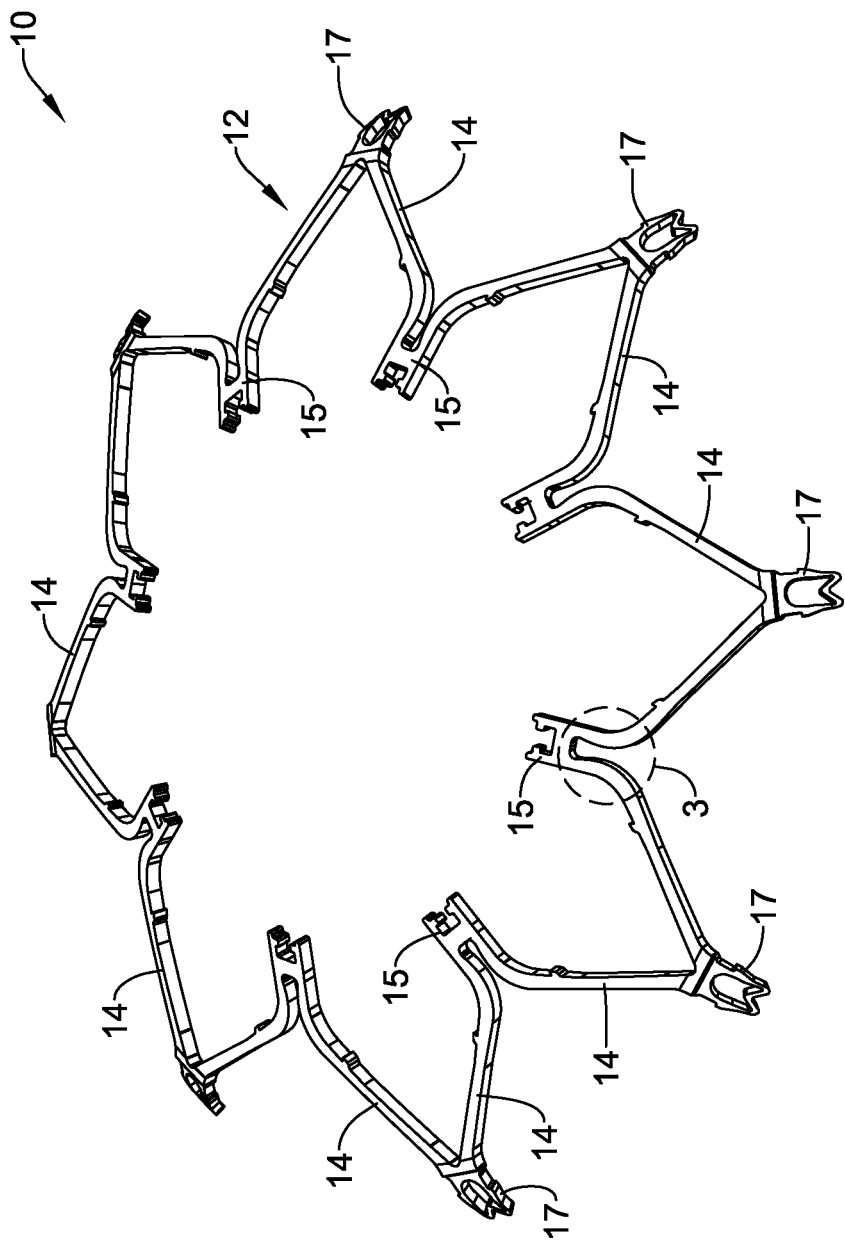
FIG. 2 is a perspective view of the frame of the example heart valve repair implant shown in FIG. 1.

FIG. 2 illustrates the frame 12 of the implant 100 shown in FIG. 1 (e.g., for simplicity, the collars 18 and anchors 16 shown in FIG. 1 have been removed from the implant 100, leaving only the bare frame 12 in FIG. 2). FIG. 2 illustrates that the struts 14 may extend around the axis 50 to form the various shapes of the frame 12. The struts 14 may be arranged such that the wall pattern of the frame 12 may be generally sinusoidally or zig-zag shaped. In some embodiments, the wall pattern may have other suitable shapes, sinusoidal or otherwise. The vertices of the sinusoidal shaped frame 12 may be pointed or rounded.

FIG. 2 illustrates that, in some examples, pairs of adjacent struts 14 may meet at an apex. For example, at least a first pair of adjacent struts 14 may meet at an upper apex or crown 15. At least a second pair of adjacent struts 14 may meets at a lower apex or crown 17. The upper and lower crowns 15, 17 are spaced sequentially along the circumference of the frame 12, with one of the upper crowns 15 followed by one of the lower crowns 17, followed by another one of the upper crowns 15, etc. In the illustrated embodiment, there are eight upper crowns 15 and eight lower crowns 17.

Referring back to FIG. 1, the upper crowns 15 may be each configured to have a collar 18 fitted over and/or around the upper crown 15. Thus, the upper crowns 15 may include various features, dimensions, etc. as described herein for coupling with the collar 18, as further described. The upper crowns 15 are shown partially covered by the collars 18 in FIG. 1. In some embodiments, one or more of the upper crowns 15 may not include a collar 18. In some embodiments, fewer than all of the upper crowns 15 may be configured to receive the collar 18. In some embodiments, all of the upper crowns 15 may be configured to receive the collar 18.

FIG. 1 further illustrates that one or more of the lower crowns 17 may be coupled with an anchor 16. Each anchor 16 may be moveably coupled with a lower crown 17, respectively. The anchor 16 may engage with tissue of the heart, for example the mitral annulus, to secure the implant 100 to the tissue of the annulus. Movement of the anchor 16 relative to the lower crowns 17 may cause the anchor 16 to penetrate the annulus tissue. The lower crowns 17 may include a variety of engagement features to allow such movement of the anchors 16, such as flanges and/or openings.

The struts 14 are reconfigurable about the upper and lower crowns 15, 17. Pairs of adjacent struts 14 that meet at the upper and lower crowns 15, 17 can move angularly relative to each other. Such movement may be described as a rotation or pivot of the adjacent struts 14 about the corresponding upper or lower crown 15, 17. For example, two adjacent struts 14 forming the upper crown 15 may be moved such that the struts 14 effectively rotate relative to each other about the upper crown 15. For example, two adjacent struts 14 forming the lower crown 17 may be moved such that the struts 14 effectively rotate relative to each other about the lower crown 17. "Rotation" of the struts 14 as described includes pinching together of the struts 14, for example with the collar 18 as described herein. Thus, adjacent struts 14 may not include an actual rotatable hinge, pin, or other rotation features. Movement of the struts 14 closer together to decrease the angle therebetween is described as a "closing" of the struts 14. Movement of the struts 14 farther apart to increase the angle therebetween is described as an "opening" of the struts 14.

The struts 14 may be biased to an enlarged cross-sectional configuration in the absence of an external force applied to the struts 14. Application of an external circumferentially compressive force to the struts 14, for example with a collar 18, may cause the struts 14 to move angularly, for example, to close. Movement of the struts 14 in this closing manner also may cause the implant 100 to decrease its circumference (e.g. diameter) in the case of a circular implant 100. In its unconstrained state, the frame 12 may be in an enlarged configuration. Application of a compressive circumferential force may cause the circumference of the frame 12 to reduce. Removal or lessening of the circumferential force may permit the frame 12 to open. The circumferential force may be increased or decreased by moving a collar 18 farther downward or upward, respectively, in the axial direction. The collar 18 may lock in place after translating axially down the upper crown 15 to secure the implant 100 at a particular width.

As described above, the implant 10 includes one or more restraints such as the collars 18. As shown in FIG. 1, the implant 10 may include eight collars 18. In some embodiments, there may be fewer or more than eight collars 18. The number of collars 18 may correspond to the number of upper crowns 15. In some embodiments, there may be fewer collars 18 than upper crowns 15. Thus, in some embodiments, some upper crowns 15 of the frame 12 may not include a collar 18

A collar 18 may couple with the corresponding upper crown 15. The collar 18 may be fitted over the upper crown 15. The collar 18 forms an inner opening at least partially therethrough and into which the upper crown 15 is received as the collar 18 fits over the upper crown 15. In some embodiments, the collars 18 may be rounded, rectangular, square, triangular, segmented, polygonal, other suitable shapes, or combinations thereof. As shown in FIG. 1, the collars 18 may at least partially surround the corresponding upper crown 15. As shown, the collars 18 completely surrounds the corresponding upper crown 15. In some embodiments the collars 18 may not completely surround the upper crown 15. The collars 18 engage with the upper crown 15.

The collars 18 may engage with and may be advanced downward over the upper crown 15 to angularly move the corresponding pair of adjacent struts 14 towards each other. The collars 18 may apply a compressive circumferential force to the struts 14 to cause the struts 14 to decrease the angle between the struts 14. The circumferential force may be applied inwardly to the struts 14 and towards the upper crowns 15. Thus, a vertical force applied to the collars 18 may be translated into a circumferential force on the struts 14. By "circumferential" it is meant that the direction of the forces is along the outer perimeter or boundary of the frame 12 as viewed from the top or bottom of the frame 12, and is not meant to limit the shape of the frame 12 to a circle. Movement of the collar 18 over the struts 14 moves, e.g. rotates, the struts 14 such that the angle between the adjacent struts 14 decreases. A first circumferential force may be applied to one of the struts 14 by a collar 18 and a second circumferential force that is opposite in direction to the first circumferential force may be applied to the adjacent strut 14 by that same collar 18. The farther the collar 18 is moved down over the struts 14, the more the struts 14 move and the more the angle decreases, causing the frame 12 to decrease in width, e.g. diameter. The struts 14 thus move relative to each other about the upper crown 15 due to movement of the collar 18. The collar 18 may lock in place, for example with a locking tab 19.

As shown in FIG. 1, the implant 10 may include one or more anchors 16. The anchors 16 may be made of a suitable biocompatible metal alloy such as stainless steel, cobalt chromium, platinum iridium, nickel titanium, other suitable materials, or combinations thereof. Each anchor 16 may be sharpened at its distal point, or leading turn, so as to facilitate penetration into the cardiac tissue. Each anchor 16 may be from about ten to about fifteen millimeters (mm) in total axial length. In some embodiments, the anchors 16 may be shorter or longer than ten to fifteen millimeters (mm) in total axial length. By "total" axial length it is meant the axial length of the anchor 16 from the end of the distal penetrating tip to the opposite, proximal end of the head. The helical portion of the anchor 16 may be from about six to about twelve millimeters (mm) in axial length, i.e. in an axial direction. In some embodiments, the helical portion of the anchor 16 may be shorter or longer than six to twelve millimeters (mm) in axial length. The anchors 16 are capable of extending from about four to about seven millimeters (mm) axially beyond the corresponding lower crown 17. For example, the helical portions of the anchors 16 may extend from four to seven millimeters (mm) into the cardiac tissue. As mentioned, the frame 12 is shown with eight upper crowns 14 and eight lower crowns 16 and anchors 16, but this number of apices is shown for illustration purposes and may be varied, for example four upper and lower apices, sixteen upper and lower apices, etc. In some embodiments, regardless of the number of apices, each upper crown 15 is fitted with a collar 18 and each lower crown 17 has a respective anchor 16 threadingly received through the openings of the anchor 16.

As described above, manipulation of one or more of the collars 18 may cinch the implant 10 such that the dimeter of the implant 10 decreases, thereby pulling the leaflets of the mitral valve closer together. However, it can be further appreciated that once the implant 10 is positioned along the mitral valve, the implant 10 may experience significant dynamic changes in its size and shape as the heart transforms through a single cardiac cycle. Further, the implant 10 will experience the dynamics changes over its lifespan, and therefore, the implant 10 needs to be designed such that it can resist the prolonged stresses associated with cyclical loading.

For example, FIG. 3 illustrates a portion of the frame 12 discussed above. In particular, FIG. 3 illustrates a curved portion 20 of a strut 14 of the frame 12. As shown in FIG. 3, the curved portion 20 of the strut 14 may be defined as generally that portion of the frame 12 where the bottom portion of the collar 18 may rest along the strut 14. It can be appreciated that as the implant 10 is cinched (via rotation of one or more collars 18), the curved portion 20 may repeatedly flex, thereby undergoing cyclical stresses over the lifespan of the implant 10. It can be appreciated that it may be beneficial to construct the implant 10 (or portions thereof, such as the curved portions 20) from materials which are designed to withstand significant cyclical loads. As discussed in greater detail below, one or more components of the implant 10 (e.g., the frame 12 or any portions thereof, such as the curved portion 20), may be constructed from specific processing methods and parameters, including, but not limited to, thermal processing and/or pre-strain processing.

The disclosure may be further clarified be reference to the following Examples, which serve to exemplify some embodiments, and not to limit the disclosure in any way.

Example 1—Example Nominal Process for Manufacturing a Nitinol Implant

An example nominal process for manufacturing a medical device, including the heart valve repair device 10 (e.g., annuloplasty ring) disclosed herein may include:

Step 1—An example nitinol specimen (e.g., frame 12) may be heat set at an initial temperature of 450° C.-550° C. for 5-20 minutes. The heat setting process may be designed to flex the nitinol specimen through multiple heating/cooling cycles to achieve specific geometries within the specimen. Additional heat exposure steps may be added to tune the austenite finish temperature or other mechanical properties of the nitinol specimen. In some instances, the final austenite finishing temperature may generally be between 15° C.-32° C.

Following the initial heat setting step (e.g., Step 1 described above), a thermo-mechanical fatigue test may be performed which may include cyclical loading of the nitinol specimen under specific loading parameters. The following paragraph provides a general description of performing the example thermo-mechanical fatigue test on a nitinol specimen.

The fatigue analysis may initially include performing a Finite Element Analysis (FEA) on a first nitinol specimen which estimates the strain values for the displacement of the specimen in a conventional cantilever test. The test may initially begin with a relatively small displacement of the specimen, whereby the specimen is subject to a predetermined number of displacement cycles (e.g., 10,000 cycles at a given amplitude). If the specimen survives the initial cyclical loading, the cantilever test may be repeated at sequentially higher amplitudes on the same specimen until the specimen breaks. After the first specimen breaks, additional nitinol specimens may be subjected to the same fatigue test using the same cyclical loading parameters and displacement sequence as the initial specimen. Each specimen may be cycled to failure and the corresponding displacement at which each specimen breaks may be determined. Thereafter, using the displacement-to-break data from the entire group of specimens, an "average displacement to break" value may be calculated. Finally, FEA analysis will be performed which may determine the strain value corresponding to the average displacement to break value determined from the entire group of nitinol samples tested. This strain value may be described as "% alternating strain."

Performing the thermo-mechanical fatigue test (described above in this Example) after the initial heat setting step (described above in this Example) may show a mean fatigue strength for a nitinol specimen of 0.498% alternating strain.

Example 2—Example Nominal Process with Pre-Strain for Manufacturing a Nitinol Implant An example nominal process with an additional pre-strain step for manufacturing a medical device, including the heart valve repair device 10 (e.g., annuloplasty ring) disclosed herein may include:

Step 1—An example nitinol specimen (e.g., annuloplasty frame 12) may be heat set at an initial temperature of 450° F.-550° F. for 5-20 minutes.

Step 2—Pre-strain the nitinol specimen utilizing mechanical or other means such that the nitinol specimen is stretched beyond the conditions for which it is designed to be used in vivo. The pre-straining step may create residual martensite and/or plastic deformation within the specimen. In some examples, the specimen may be pre-strained between 1-100 cycles. In some examples, the pre-straining of the specimen may be performed at a strain amplitude of between 4-16%.

After the processing steps described above are completed, the fatigue test (described with respect to Example 1 may be performed). The fatigue test results of the nominal process (described above with respect to Example 1) with the additional pre-strain step (described above in this Example) may show a mean fatigue strength for a nitinol specimen of 0.822% alternating strain. This represents a percentage increase of 65% over the nominal process (e.g., 0.822% vs. 0.498% alternating strain).

Example 3—Example Nominal Process With R-Phase Processing for Manufacturing a Nitinol Implant An example nominal process with a R-phase processing step for manufacturing a medical device, including the heart valve repair device 10 (e.g., annuloplasty ring) disclosed herein may include:

Step 1—An example nitinol specimen (e.g., annuloplasty frame 12) may be heat set at an initial temperature of 450° F.-550° F. for 5-20 minutes.

Step 2—Heat set the nitinol implant to develop R-phase. The R-phase processing may include heat setting the specimen at 150° C.-350° C. for 6-720 hours after the final shape setting has been achieved.

After the processing steps described above are completed, the fatigue test (described above with respect to Example 1 may be performed). The fatigue test results of the nominal process (described above with respect to Example 1) with R-phase processing (described above in this Example) may show a mean fatigue strength for the specimen of 0.761% alternating strain. This represents a percentage increase of 53% over the nominal process (e.g., 0.761% vs. 0.498% alternating strain).

Example 4—Example Nominal Process with Both Pre-Strain Processing and R-Phase Processing for Manufacturing a Nitinol Implant An example nominal process with a R-phase processing step for manufacturing a medical device, including the heart valve repair device 10 (e.g., annuloplasty ring) disclosed herein may include:

Step 1—An example nitinol specimen (e.g., annuloplasty frame 12) may be heat set at an initial temperature of 450° F.-550° F. for 5-20 minutes.

Step 2—Heat set the nitinol implant to develop R-phase. The R-phase processing may include heat setting the implant at 150° C.-350° C. for 6-720 hours after the final shape setting has been achieved.

Step 3—Pre-strain the nitinol specimen between 1-100 cycles. In some examples, the pre-straining of the specimen may be performed at a strain amplitude of between 4-16%.

Processing the nitinol implant utilizing both R-phase processing and pre-strain processing may change the dislocation density and microstructure of the implant and may increase the fatigue resistance of the device.

After the processing steps described above are completed, the fatigue test (described above respect to Examples 1) may be performed. The fatigue test results of the nominal process with both R-phase processing and pre-strain processing may show a mean fatigue strength for the specimen of 1.48% alternating strain. This represents a percentage increase of 197% over the nominal process (e.g., 1.48% vs. 0.498% alternating strain).

The materials that can be used for the various components of medical device 10 may include those commonly associated with medical devices. For simplicity purposes, the following discussion refers to the implant 10 and other components of the implant 10. However, this is not intended to limit the devices and methods described herein, as the discussion may be applied to other medical devices disclosed herein.

The medical device 10 and/or other components of the medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the implant 10 to achieve the same result.

In some embodiments, a degree of Magnetic Resonance Imaging (MRI) compatibility is imparted into the implant 10. For example, the medical device 10, or portions thereof, may be made of a material that does not substantially distort the image and create substantial artifacts (e.g., gaps in the image). Certain ferromagnetic materials, for example, may not be suitable because they may create artifacts in an MRI image. The implant 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. A method of forming a medical device, the method comprising:
    forming a nickel-titanium alloy into a fatigue resistant frame; and
    heat setting the frame between a temperature of 150-350 degrees Celsius over a time period of from 24 to 105 hours.

2. The method of claim 1, further comprising flexing the frame between 10-100 pre-strain cycles.

3. The method of claim 2, wherein flexing the frame between 10-100 pre-strain cycles further includes flexing the frame at a strain amplitude of between 6-12%.

4. The method of claim 1, wherein heat setting the frame between a temperature of 150-350 degrees Celsius over a time period of from 24 to 105 hours induces the nickel-titanium alloy to have a R-phase when the frame is at a temperature between 35-39 degrees Celsius.

* * * * *